US012268820B2

(12) United States Patent
Liu et al.

(10) Patent No.: US 12,268,820 B2
(45) Date of Patent: Apr. 8, 2025

(54) NON-HYSTERETIC OXYGEN SUPPLY RESPIRATOR SYSTEM

(71) Applicant: Hunan Ventmed Medical Technology Co., Ltd., Shaoyang (CN)

(72) Inventors: Zhe Liu, Shaoyang (CN); Lei Zhou, Shaoyang (CN); Congneng Tang, Shaoyang (CN); Qichang Zheng, Shaoyang (CN); Jinping Su, Shaoyang (CN); Zaixin Yuan, Shaoyang (CN)

(73) Assignee: Hunan Ventmed Medical Technology Co., Ltd., Shaoyang (CN)

( * ) Notice: Subject to any disclaimer, the term of this patent is extended or adjusted under 35 U.S.C. 154(b) by 702 days.

(21) Appl. No.: 17/670,552

(22) Filed: Feb. 14, 2022

(65) Prior Publication Data
US 2022/0305230 A1   Sep. 29, 2022

Related U.S. Application Data

(63) Continuation of application No. PCT/CN2021/136371, filed on Dec. 8, 2021.

(30) Foreign Application Priority Data

Mar. 25, 2021   (CN) .......................... 202110319087.9

(51) Int. Cl.
*A61M 16/20* (2006.01)
*A61M 16/00* (2006.01)
*A61M 16/10* (2006.01)

(52) U.S. Cl.
CPC ...... *A61M 16/208* (2013.01); *A61M 16/0003* (2014.02); *A61M 16/1005* (2014.02);
(Continued)

(58) Field of Classification Search
CPC ............ A61M 16/208; A61M 16/0003; A61M 16/1005; A61M 16/201;
(Continued)

(56) References Cited

U.S. PATENT DOCUMENTS

| 6,675,798 B1 * | 1/2004 | Tyomkin ............. A61M 16/022 |
| | | 128/204.23 |
| 2005/0133024 A1 * | 6/2005 | Coifman ................ A61B 5/087 |
| | | 128/200.14 |

(Continued)

FOREIGN PATENT DOCUMENTS

| CN | 101310791 A | * 11/2008 |
| CN | 109069778 A | 12/2018 |

(Continued)

OTHER PUBLICATIONS

Hermann Neinhaus, Electronic excitations by chemical reactions on metal surfaces, 2002, Elsevier (Year: 2002).*

*Primary Examiner* — Brandy S Lee
*Assistant Examiner* — Melis T. Jensen
(74) *Attorney, Agent, or Firm* — Sang Young Han (57) ABSTRACT

The present invention discloses a non-hysteretic oxygen supply respirator system, comprising a respiratory mask, an inhaling pipe, an exhaling pipe, an oxygen supply chamber, an auxiliary oxygen supply pipeline, and a start-stop cylinder for opening and closing the auxiliary oxygen supply pipeline. The non-hysteretic oxygen supply respirator system in the present invention supplies a small amount of oxygen during the second half of exhaling by providing the auxiliary oxygen supply pipeline, so as to compensate for the amount of oxygen required by a user during the hysteretic time after the respirator senses the inhaling airflow, avoid the situation that the user inhales laboriously due to the hysteresis of inhaling oxygen supply, and give the user a better respiratory experience. The start and stop of the (Continued)

auxiliary oxygen supply pipeline are controlled by the airflow of the exhaling pipe, making the control simple and convenient and the exhaling smoother.

7 Claims, 7 Drawing Sheets

(52) U.S. Cl.
CPC ............... *A61M 2016/0042* (2013.01); *A61M 2205/0216* (2013.01)

(58) Field of Classification Search
CPC ....... A61M 16/0883–0891; A61M 2016/0042; A61M 2205/0216; A61M 2205/3331; A61M 2202/0208
See application file for complete search history.

(56) References Cited

U.S. PATENT DOCUMENTS

| | | | |
|---|---|---|---|
| 2010/0043796 | A1 | 2/2010 | Meynink et al. |
| 2010/0170512 | A1* | 7/2010 | Kuypers ........... A61M 16/0069 128/204.23 |
| 2013/0228180 | A1 | 9/2013 | Ahmad et al. |
| 2020/0188615 | A1* | 6/2020 | Troili ................ A61M 16/0069 |
| 2021/0080311 | A1* | 3/2021 | Beacham ................ G01F 25/10 |

FOREIGN PATENT DOCUMENTS

| | | | |
|---|---|---|---|
| CN | 109475762 A | | 3/2019 |
| CN | 111973855 A | | 11/2020 |
| CN | 214158315 U | * | 9/2021 |

* cited by examiner

NON-HYSTERETIC OXYGEN SUPPLY RESPIRATOR SYSTEM

CROSS-REFERENCE TO RELATED APPLICATIONS

The application claims priority to Chinese patent application No. 2021103190879, filed on Mar. 25, 2021, the entire contents of which are incorporated herein by reference.

TECHNICAL FIELD

The present invention relates to the technical field of respirators, and more particularly to a non-hysteretic oxygen supply respirator system.

BACKGROUND

A respirator is a device that can replace, control, or change the normal physiological respiration of human beings, increase lung ventilation amount, improve respiratory function, reduce respiratory work consumption, and save cardiac reserve capacity.

When the auxiliary respiration is triggered by airflow, the respirator can keep working synchronously with the patient's inhaling so as to facilitate the withdrawal of the respirator. However, due to the limitation of the airflow detection synchronization device, when the patient starts to inhale, the respirator shall be delayed for about 20 ms to synchronize, thereby forming the hysteresis of respiration and oxygen supply. The faster the patient's respiratory frequency is, the longer the respirator delays, and the more the patient's respiratory work is, resulting in poor respiratory experience.

SUMMARY

It is an object of the present invention to address the problem of oxygen supply hysteresis in respirators in the prior art and to provide a non-hysteretic oxygen supply respirator system for improving the phenomenon of oxygen supply hysteresis in respirators.

In order to achieve the above object, the invention adopts the following technical solution.

A non-hysteretic oxygen supply respirator system comprises a respiratory mask, an inhaling pipe, an exhaling pipe, an oxygen supply chamber, an auxiliary oxygen supply pipeline, and a start-stop cylinder for opening and closing the auxiliary oxygen supply pipeline. The respiratory mask and the oxygen supply chamber are in communication respectively via the inhaling pipe and the auxiliary oxygen supply pipeline. The oxygen supply chamber is used for providing an oxygen gas with suitable oxygen content. One end of the exhaling pipe is connected to the respiratory mask, and the other end of the exhaling pipe is connected to an air outlet pipe. The respiratory mask is in communication with the outside via the exhaling pipe. An inhaling airflow sensor is provided inside the respiratory mask, and an electrically controlled inhaling valve is provided on the inhaling pipe. When the inhaling of a user is sensed, the inhaling valve is opened. The user inhales through the inhaling pipe and exhales through the exhaling pipe. A check valve is provided on the exhaling pipe to prevent the airflow of the exhaling pipe from flowing in reverse.

Further, the auxiliary oxygen supply pipe and the exhaling pipe pass through the start-stop cylinder. Inside the start-stop cylinder, the auxiliary oxygen supply pipe is spirally wound outside the exhaling pipe; a branch pipe is provided between the exhaling pipe and the auxiliary oxygen supply pipe; one end of the branch pipe is in communication with the exhaling pipe, and the other end of the branch pipe is provided in a sealed manner; a piston and one end of a connecting rod are provided inside the branch pipe, the connecting rod extending from the sealed end of the branch pipe.

Further, a slideway, a support seat, and a pressing block are provided inside the start-stop cylinder. The spiral part of the auxiliary oxygen supply pipeline is located between the support seat and the pressing block, the slideway and the support seat are fixedly connected to the inner wall of the start-stop cylinder, the pressing block is fixedly connected to one end of the connecting rod outside the branch pipe, and the pressing block is slidably connected to the start-stop cylinder via the slideway. In the above-mentioned structure, the pressing block approaches in the direction of the support seat so that the spiral part of the spiral part of the auxiliary oxygen supply pipe can be squeezed and the spiral part of the auxiliary oxygen supply pipe can be intercepted. The auxiliary oxygen supply pipe inside the start-stop cylinder is a thin-walled flexible pipe, and the wall thickness of the auxiliary oxygen supply pipe satisfies the pressure of the pressing block so that the pipe wall can be adhered to the support seat to achieve interception so as to avoid the influence of the oxygen airflow of the auxiliary oxygen supply pipe on exhaling.

Preferably, the auxiliary oxygen supply pipe is provided with an arc-shaped elastic support rod and an elastic isolating block inside the pipeline between the support seat and the pressing block. The isolating block is located in the middle of the auxiliary oxygen supply pipeline, and two elastic support rods are symmetrically distributed on two sides of the isolating block; when the pressing block presses towards the support seat, the isolating block is elongated with the aid of the elastic support rod, and the isolating block is pressed between the pressing block and the support seat; when there is a gap between the isolating block and the pressing block and the support seat, the auxiliary oxygen supply pipeline is intercepted. When the pressing block leaves the support seat, the elastic support rod and the isolating block can rebound to support the auxiliary oxygen supply pipe, maintain the normal circulation of the auxiliary oxygen supply pipe, and reduce the deformation or breakage of the auxiliary oxygen supply pipe due to the pressing.

Preferably, the material of the elastic support rod is an electrified and exothermic metal, and both ends of the elastic support rod are connected to a leading wire for electrification. The electrified and exothermic elastic support rod can heat the gas in the auxiliary oxygen supply pipe to enhance the use experience. When the auxiliary oxygen supply pipe is intercepted, the elastic support rod is integrally located at the side face of the isolating block, preventing the elastic support rod from being directly squeezed by the pressing block and the support seat, and preventing the elastic support rod from being damaged by squeezing.

Further, the branch pipe is provided with a start-stop valve and a driving fan, the start-stop valve being located between the piston and the driving fan. The start-stop valve comprises a circulation seat, a sliding ring, a cover plate, a return spring, a circulation sliding block, and an exhaust pipe. The circulation seat and the sliding ring are fixedly located on the inner wall of the branch pipe, the circulation sliding block is fixedly connected to the cover plate via a rod member, the cover plate is located between the circulation seat and the sliding ring, the return spring is provided between the cover plate and the sliding ring, the circulation sliding block is located inside the sliding ring and is in sliding and sealing connection with the sliding ring, the circulation sliding block is provided with a circulation hole, and the exhaust pipe is located on one side (left side) of the sliding ring close to the piston.

An airflow sensor is provided inside the exhaling pipe in the present invention. When the airflow sensor in the exhaling pipe senses the exhaled airflow, the driving fan is driven to rotate. The rotation of the driving fan can accelerate the airflow of the exhaling of the exhaling pipe, and at the same time, the air out end of the driving fan is aligned with the circulation seat; the airflow generated by the driving fan can blow the cover plate so that the cover plate and the circulation seat generate a gap; at the same time, the side face of the circulation sliding block covers the exhaust pipe so that the airflow blows through the gap, and passes through the circulation hole of the circulation sliding block to push the piston to move, thereby the pressing block moving closer to the direction of the support seat; when the piston reaches the limit position, the auxiliary oxygen supply pipeline is intercepted, and at this time, the exhaust pipe is located on the right side of the circulation sliding block and is opened, and the air at the air out end of the driving fan is discharged from the exhaust pipe. When the exhaling is weakened, the driving fan stops working. The cover plate and the circulation sliding block return under the drive of the return spring. The exhaust pipe is located on the left side of the circulation sliding block and is opened. The pressing block and the piston return under the push of the airflow inside the auxiliary oxygen supply pipe, the elastic support member, and the isolating block. The auxiliary oxygen supply pipe is conducted, and the auxiliary oxygen supply pipe supplies oxygen to the respiratory mask. During the return of the piston, the gas between the piston and the cover plate is discharged from the exhaust pipe.

The auxiliary oxygen supply pipe is provided with a pressure reducing valve for reducing the flow rate of the oxygen in the auxiliary oxygen supply pipe to avoid oxygen poisoning caused by excessive oxygen supply.

The present invention has beneficial effects as follows.

1. The non-hysteretic oxygen supply respirator system supplies a small amount of oxygen during the second half of exhaling by providing the auxiliary oxygen supply pipeline so as to compensate for the amount of oxygen required by a user during the hysteretic time after the respirator senses the inhaling airflow, avoid the situation that the user inhales laboriously due to the hysteresis of inhaling oxygen supply, and give the user a better respiratory experience.

2. The non-hysteretic oxygen supply respirator system controls the start and stop of the auxiliary oxygen supply pipeline via the airflow of the exhaling pipe, making the control simple and convenient. It can accelerate the exhausting rate of the exhaling pipeline, and provide a low-pressure exhaling environment for the user to exhale, making exhaling smoother.

3. The auxiliary oxygen supply pipeline of the non-hysteretic oxygen supply respirator system is provided with an elastic support member and an isolating block for returning in the inside so that the auxiliary oxygen supply pipeline can quickly resume circulation after being intercepted, and at the same time, the gas in the auxiliary oxygen supply pipeline can be heated to make respiration more comfortable.

DETAILED DESCRIPTION OF THE EMBODIMENTS

The technical solutions in the embodiments of the present invention will be clearly and completely described below in conjunction with the accompanying drawings in the embodiments of the present invention. Obviously, the described embodiments are only a part of the embodiments of the present invention, rather than all the embodiments.

Figure 1:
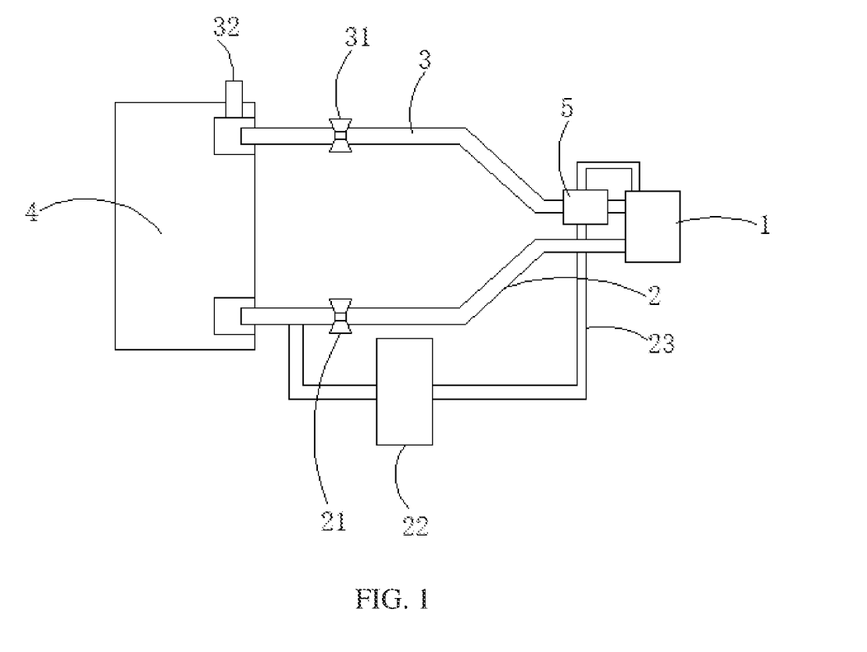
FIG. 1 is a system connection diagram of a non-hysteretic oxygen supply respirator system.

With reference to FIG. 1, a non-hysteretic oxygen supply respirator system comprises a respiratory mask 1, an inhaling pipe 2, an exhaling pipe 3, an oxygen supply chamber 4, an auxiliary oxygen supply pipeline 23, and a start-stop cylinder 5 for opening and closing the auxiliary oxygen supply pipeline 23. The respiratory mask 1 and the oxygen supply chamber 4 are in communication respectively via the inhaling pipe 2 and the auxiliary oxygen supply pipeline 23. The oxygen supply chamber 4 is used for providing an oxygen gas with suitable oxygen content. One end of the exhaling pipe 3 is connected to the respiratory mask 1, and the other end of the exhaling pipe 3 is connected to an air outlet pipe 32. The respiratory mask 1 is in communication with the outside via the exhaling pipe 3. An inhaling airflow sensor is provided inside the respiratory mask 1, and an electrically controlled inhaling valve 21 is provided on the inhaling pipe 2. When the inhaling of a user is sensed, the inhaling valve 21 is opened. The user inhales through the inhaling pipe 2 and exhales through the exhaling pipe 3. A check valve 31 is provided on the exhaling pipe 3 to prevent the airflow of the exhaling pipe 3 from flowing in reverse.

Figure 2:
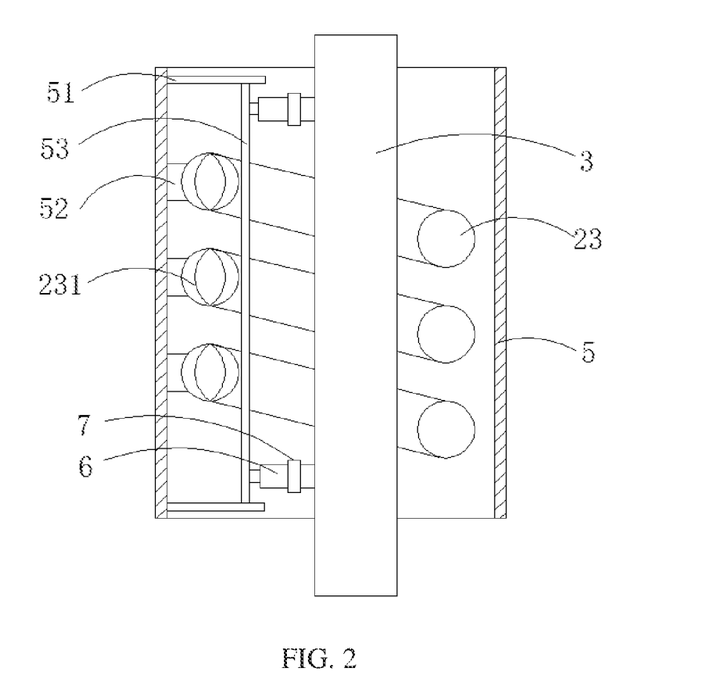
FIG. 2 is a schematic view of a structure of a start-stop cylinder of the non-hysteretic oxygen supply respirator system.
Figure 3:
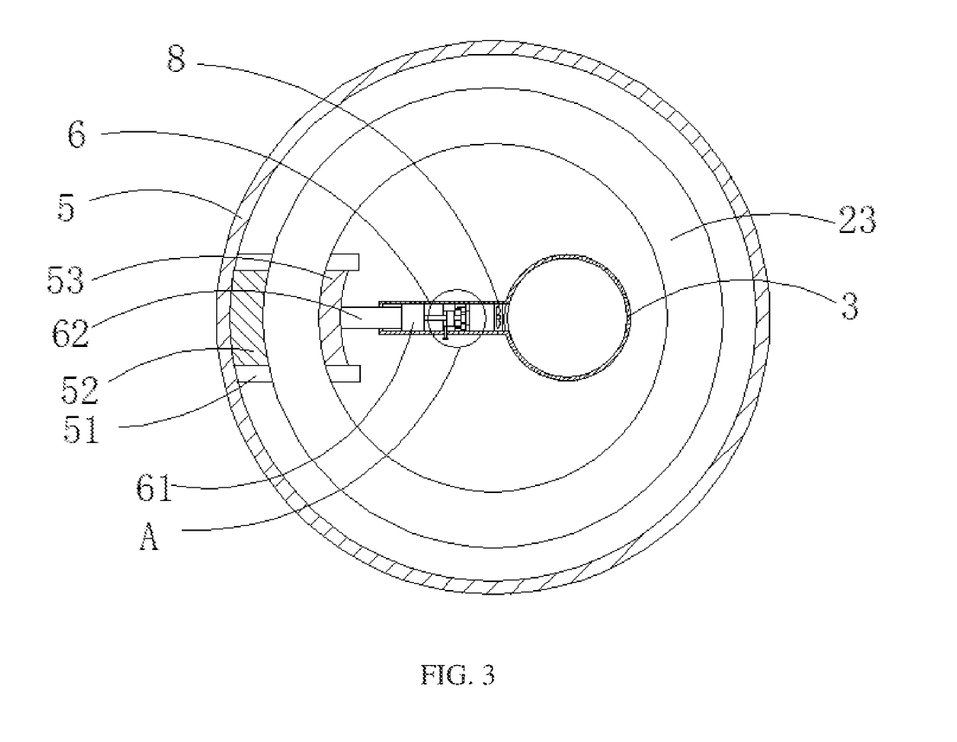
FIG. 3 is a radial cross-sectional view of a start-stop cylinder of the non-hysteretic oxygen supply respirator system.
Figure 4:
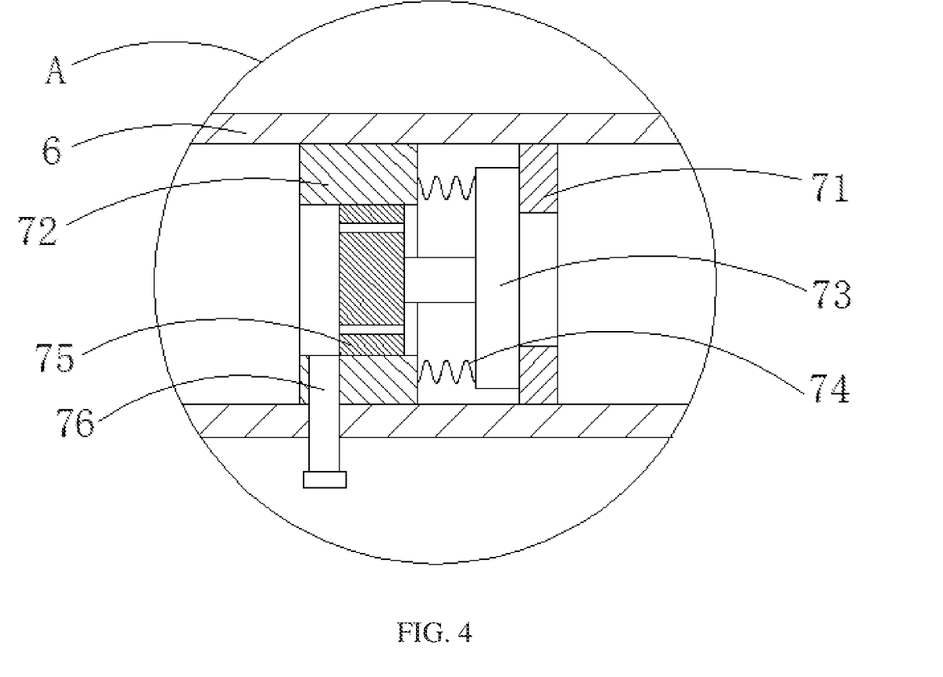
FIG. 4 is an enlarged view at the radial cross-sectional A of a start-stop cylinder of the non-hysteretic oxygen supply respirator system.

Further, the auxiliary oxygen supply pipeline 23 and the exhaling pipe 3 pass through the start-stop cylinder 5. With reference to FIGS. 2, 3, and 4, inside the start-stop cylinder 5, the auxiliary oxygen supply pipeline 23 is spirally wound outside the exhaling pipe 3; a branch pipe 6 is provided between the exhaling pipe 3 and the auxiliary oxygen supply pipeline 23; one end of the branch pipe 6 is in communication with the exhaling pipe 3, and the other end of the branch pipe 6 is provided in a sealed manner; a piston 61 and one end of a connecting rod 62 are provided inside the branch pipe 6, the connecting rod 62 extending from the sealed end of the branch pipe 6.

Further, a slideway 51, a support seat 52, and a pressing block 53 are provided inside the start-stop cylinder 5. The spiral part of the auxiliary oxygen supply pipeline 23 is located between the support seat 52 and the pressing block 53, the slideway 51 and the support seat 52 are fixedly connected to the inner wall of the start-stop cylinder 5, the pressing block 53 is fixedly connected to one end of the connecting rod 62 outside the branch pipe 6, and the pressing block 53 is slidably connected to the start-stop cylinder 5 via the slideway 51. In the above-mentioned structure, the pressing block 53 approaches in the direction of the support seat 52 so that the spiral part of the auxiliary oxygen supply pipeline 23 can be squeezed and the spiral part of the auxiliary oxygen supply pipeline 23 can be intercepted. The auxiliary oxygen supply pipeline 23 inside the start-stop cylinder 5 is a thin-walled flexible pipe, and the wall thickness of the auxiliary oxygen supply pipeline 23 satisfies the pressure of the pressing block 53 so that the pipe wall can be adhered to the support seat 52 to achieve interception so as to avoid the influence of the oxygen airflow of the auxiliary oxygen supply pipeline 23 on exhaling.

Figure 5:
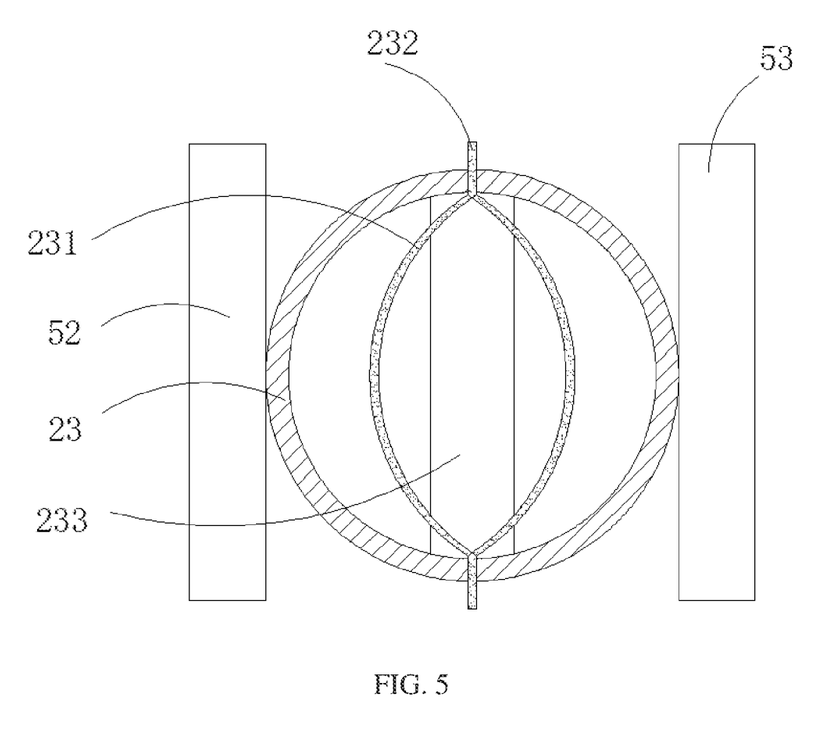
FIG. 5 is a schematic view of a structure of an auxiliary oxygen supply pipeline of the non-hysteretic oxygen supply respirator system.

In this embodiment, referring to FIG. 5, the auxiliary oxygen supply pipeline 23 is provided with an arc-shaped elastic support rod 231 and an elastic isolating block 233 inside the pipeline between the support seat 52 and the pressing block 53. The isolating block 233 is located in the middle of the auxiliary oxygen supply pipeline 23, and two elastic support rods 231 are symmetrically distributed on two sides of the isolating block 233; when the pressing block 53 presses towards the support seat 52, the isolating block 233 is elongated with the aid of the elastic support rod 231, and the isolating block 233 is pressed between the pressing block 53 and the support seat 52; when there is a gap between the isolating block 233 and the pressing block 53 and the support seat 52, the auxiliary oxygen supply pipeline 23 is intercepted. When the pressing block 53 leaves the support seat 52, the elastic support rod 231 and the isolating block 233 can rebound to support the auxiliary oxygen supply pipeline 23, maintain the normal circulation of the auxiliary oxygen supply pipeline 23, and reduce the deformation or breakage of the auxiliary oxygen supply pipeline 23 due to the pressing.

Further, the material of the elastic support rod 231 is an electrified and exothermic metal, and both ends of the elastic support rod 231 are connected to a leading wire 232 for electrification. The electrified and exothermic elastic support rod 231 can heat the gas in the auxiliary oxygen supply pipeline 23 to enhance the use experience. When the auxiliary oxygen supply pipeline 23 is intercepted, the elastic support rod 231 is integrally located at the side face of the isolating block 233, preventing the elastic support rod 231 from being directly squeezed by the pressing block 53 and the support seat 52, and preventing the elastic support rod 231 from being damaged by squeezing.

Further, the branch pipe 6 is provided with a start-stop valve 7 and a driving fan 8, the start-stop valve 7 being located between the piston 61 and the driving fan 8. The start-stop valve 7 comprises a circulation seat 71, a sliding ring 72, a cover plate 73, a return spring 74, a circulation sliding block 75, and an exhaust pipe 76. The circulation seat 71 and the sliding ring 72 are fixedly located on the inner wall of the branch pipe 6, the circulation sliding block 75 is fixedly connected to the cover plate 73 via a rod member, the cover plate 73 is located between the circulation seat 71 and the sliding ring 72, the return spring 74 is provided between the cover plate 73 and the sliding ring 72, the circulation sliding block 75 is located inside the sliding ring 72 and is in sliding and sealing connection with the sliding ring 72, the circulation sliding block 75 is provided with a circulation hole, and the exhaust pipe 76 is located on one side (left side) of the sliding ring 72 close to the piston 61.

An airflow sensor is provided inside the exhaling pipe 3 in this embodiment. When the airflow sensor in the exhaling pipe 3 senses the exhaled airflow, the driving fan 8 is driven to rotate. The rotation of the driving fan 8 can accelerate the airflow of the exhaling of the exhaling pipe 3, and at the same time, the air out end of the driving fan 8 is aligned with the circulation seat 71; the airflow generated by the driving fan 8 can blow the cover plate 73 so that the cover plate 73 and the circulation seat 71 generate a gap; at the same time, the side face of the circulation sliding block 75 covers the exhaust pipe 76 so that the airflow blows through the gap, and passes through the circulation hole of the circulation sliding block 75 to push the piston 62 to move, thereby the pressing block 53 moving closer to the direction of the support seat 52; when the piston 62 reaches the limit position, the auxiliary oxygen supply pipeline 23 is intercepted, and at this time, the exhaust pipe 76 is located on the right side of the circulation sliding block 75 and is opened, and the air at the air out end of the driving fan 8 is discharged from the exhaust pipe 76. When the exhaling is weakened, the driving fan 8 stops working. The cover plate 73 and the circulation sliding block 75 return under the drive of the return spring 74. The exhaust pipe 76 is located on the left side of the circulation sliding block 75 and is opened. The pressing block 53 and the piston 62 return under the push of the airflow inside the auxiliary oxygen supply pipeline 23, the elastic support member 231, and the isolating block 233. The auxiliary oxygen supply pipeline 23 is conducted, and the auxiliary oxygen supply pipeline 23 supplies oxygen to the respiratory mask 1. During the return of the piston 62, the gas between the piston 62 and the cover plate 73 is discharged from the exhaust pipe 76.

The auxiliary oxygen supply pipeline 23 is provided with a pressure reducing valve 22 for reducing the flow rate of the oxygen in the auxiliary oxygen supply pipeline 23 to avoid oxygen poisoning caused by excessive oxygen supply.

The working process of the compensated respirator in this embodiment is as follows.

Step 1: a user puts on a respiratory mask 1, the user inhales, an inhaling airflow sensor inside the respiratory mask 1 senses the inhaling airflow, an electrically controlled inhaling valve 21 on an inhaling pipe 2 opens, and the user inhales via the inhaling pipe 2.

Step 2: after the inhaling is completed, the user exhales, and the gas exhaled by the user is discharged from the exhaling pipe 3; when the airflow sensor in the exhaling pipe 3 senses the exhaled airflow, the controller drives the fan 8 to be driven to rotate;

the rotation of the driving fan 8 can accelerate the airflow of the exhaling of the exhaling pipe 3, give the user a low-pressure pipeline environment required for exhaling, and make the exhaling smoother; at the same time, the air out end of the driving fan 8 is aligned with the circulation seat 71; the airflow generated by the driving fan 8 can blow the cover plate 73 so that the cover plate 73 and the circulation seat 71 generate a gap; at the same time, the side face of the circulation sliding block 75 covers the exhaust pipe 76 so that the airflow blows through the gap, and passes through the circulation hole of the circulation sliding block 75 to push the piston 62 to move, thereby the pressing block 53 moving closer to the direction of the support seat 52; when the piston 62 reaches the limit position, the auxiliary oxygen supply pipeline 23 is intercepted, and the pure exhaling state is entered; at this time, the exhaust pipe 76 is located on the right side of the circulation sliding block 75 and is opened, and the air at the air out end of the driving fan 8 is discharged from the exhaust pipe 76.

Step 3: when the exhaling is weakened, the airflow sensor senses the weakened exhaling airflow, and the controller drives the fan 8 to stop working; the cover plate 73 and the circulation sliding block 75 return under the drive of the return spring 74; the exhaust pipe 76 is located on the left side of the circulation sliding block 75 and is opened; the pressing block 53 and the piston 62 return under the push of the airflow inside the auxiliary oxygen supply pipeline 23, the elastic support member 231, and the isolating block 233; the auxiliary oxygen supply pipeline 23 is conducted, and the auxiliary oxygen supply pipeline 23 supplies oxygen to the respiratory mask 1; this oxygen supply action is located before the user inhales for advancing the presence of oxygen inside the respiratory mask 1 to compensate for the delayed opening of the inhaling valve 21.

Step 4: when exhaling is completed, the user inhales, the inhaling airflow sensor inside the respiratory mask 1 senses the inhaling airflow, the electrically controlled inhaling valve 21 on the inhaling pipe 2 opens, and the user inhales via the inhaling pipe 2.

Figure 6:
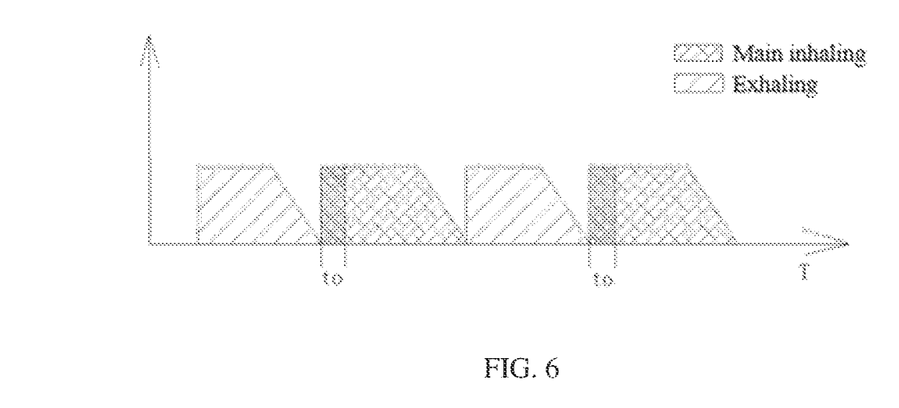
FIG. 6 is a schematic view of respiratory airflow of a respirator in the prior art.
Figure 7:
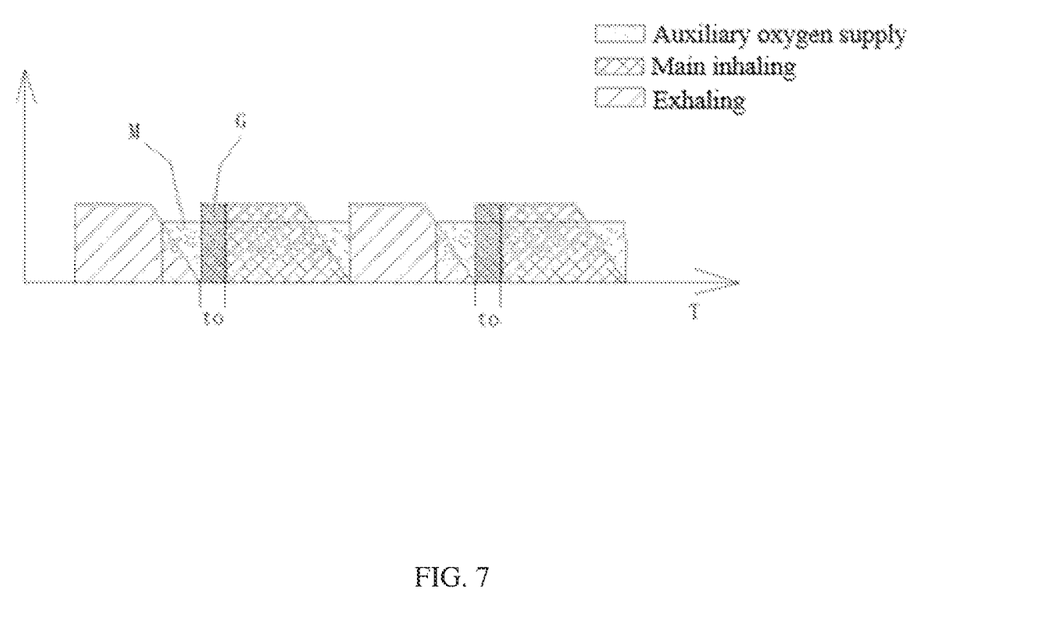
FIG. 7 is a schematic view of respiratory airflow of the non-hysteretic oxygen supply respirator system.

Referring to FIG. 6, a process of the respiratory airflow of a respirator in the prior art is shown, where to corresponds to an oxygen supply hysteretic time during which the user is substantially in the inhaling state, but the machine cannot normally supply oxygen. With reference to FIG. 7, a process of respiratory airflow of the non-hysteretic oxygen supply respirator system is shown. In the second half of the exhaling stage, the auxiliary oxygen supply pipeline 23 starts to supply oxygen. Wherein the oxygen supply amount M of the auxiliary oxygen supply pipeline 23 is not less than the oxygen shortage amount G corresponding to the oxygen supply hysteretic time to so as to realize the sufficient compensation for oxygen, improve the laborious inhaling condition, and give the user a better respiratory experience.

The above are only preferred specific implementation modes of the present invention, and the scope of the present invention is not limited thereto. Equivalent replacements or changes made by any technician familiar with the technical field according to the technical solution of the present invention and its inventive concept within the technical scope disclosed by the present invention shall be covered by the scope of the present invention.

What is claimed is:

1. A non-hysteretic oxygen supply respirator system, comprising a respiratory mask (1), an inhaling pipe (2), an exhaling pipe (3), an oxygen supply chamber (4), an auxiliary oxygen supply pipeline (23), and a start-stop cylinder (5) for opening and closing the auxiliary oxygen supply pipeline (23), wherein the respiratory mask (1) and the oxygen supply chamber (4) are in communication respectively via the inhaling pipe (2) and the auxiliary oxygen supply pipeline (23), the respiratory mask (1) is in communication with outside via the exhaling pipe (3), and the auxiliary oxygen supply pipeline (23) and the exhaling pipe (3) pass through the start-stop cylinder (5);

the auxiliary oxygen supply pipeline (23) is spirally wound outside the exhaling pipe (3), a branch pipe (6) is provided between the exhaling pipe (3) and the auxiliary oxygen supply pipeline (23), a piston (61) and one end of a connecting rod (62) are provided inside the branch pipe (6), and the connecting rod (62) extends from the branch pipe (6);

a slideway (51), a support seat (52), and a pressing block (53) are provided inside the start-stop cylinder (5); a spiral part of the auxiliary oxygen supply pipeline (23) is located between the support seat (52) and the pressing block (53), the slideway (51) and the support seat (52) are fixedly connected to an inner wall of the start-stop cylinder (5), the pressing block (53) is fixedly connected to one end of the connecting rod (62) outside the branch pipe (6), and the pressing block (53) is slidably connected to the start-stop cylinder (5) via the slideway (51);

the auxiliary oxygen supply pipeline (23) is provided with an arc-shaped elastic support rod (231) and an elastic isolating block (233) inside a pipeline between the support seat (52) and the pressing block (53).

2. The non-hysteretic oxygen supply respirator system of claim 1, wherein the branch pipe (6) is provided with a start-stop valve (7) and a driving fan (8), the start-stop valve (7) being located between the piston (61) and the driving fan (8);

the start-stop valve (7) comprises a circulation seat (71), a sliding ring (72), a cover plate (73), a return spring (74), a circulation sliding block (75), and an exhaust pipe (76); the circulation seat (71) and the sliding ring (72) are fixedly located on the inner wall of the branch pipe (6), the circulation sliding block (75) is fixedly connected to the cover plate (73) via a rod member, the cover plate (73) is located between the circulation seat (71) and the sliding ring (72), a return spring (74) is provided between the cover plate (73) and the sliding ring (72), the circulation sliding block (75) is located inside the sliding ring (72) and is in sliding and sealing connection with the sliding ring (72), the circulation sliding block (75) is provided with a circulation hole, and the exhaust pipe (76) is located on one side of the sliding ring (72) close to the piston (61).

3. The non-hysteretic oxygen supply respirator system of claim 1, wherein a material of the elastic support rod (231) is an electrified and exothermic metal, and both ends of the elastic support rod (231) are connected to a leading wire (232) for electrification.

4. The non-hysteretic oxygen supply respirator system of claim 2, wherein a material of the elastic support rod (231) is an electrified and exothermic metal, and both ends of the elastic support rod (231) are connected to a leading wire (232) for electrification.

5. The non-hysteretic oxygen supply respirator system of claim 3, wherein the respiratory mask (1) and the exhaling pipe (3) are internally provided with an airflow sensor.

6. The non-hysteretic oxygen supply respirator system of claim 3, wherein a check valve (31) is provided on the exhaling pipe (3).

7. The non-hysteretic oxygen supply respirator system of claim 3, wherein a pressure reducing valve (22) is provided on the auxiliary oxygen supply pipeline (23).

\* \* \* \* \*